(12) United States Patent
Steiner et al.

(10) Patent No.: US 8,796,169 B2
(45) Date of Patent: Aug. 5, 2014

(54) CATALYST FOR SELECTIVE METHANIZATION OF CARBON MONOXIDE

(75) Inventors: Jochen Steiner, Mannheim (DE); Markus Hoelzle, The Woodlands, TX (US); Heiko Urtel, Mannheim (DE)

(73) Assignee: BASF SE, Ludwigshafen (DE)

( * ) Notice: Subject to any disclaimer, the term of this patent is extended or adjusted under 35 U.S.C. 154(b) by 367 days.

(21) Appl. No.: 12/527,433

(22) PCT Filed: Feb. 15, 2008

(86) PCT No.: PCT/EP2008/051862
§ 371 (c)(1), (2), (4) Date: Aug. 17, 2009

(87) PCT Pub. No.: WO2008/101875
PCT Pub. Date: Aug. 28, 2008

(65) Prior Publication Data
US 2010/0093525 A1     Apr. 15, 2010

(30) Foreign Application Priority Data
Feb. 23, 2007   (EP) .................................... 07102945

(51) Int. Cl.
B01J 23/00     (2006.01)
B01J 23/08     (2006.01)
B01J 23/63     (2006.01)
C07C 1/04      (2006.01)

(52) U.S. Cl.
CPC ............... B01J 23/63 (2013.01); B01J 23/002 (2013.01); C07C 1/0435 (2013.01)
USPC ........... 502/303; 502/304; 502/325; 502/349; 502/351; 502/355

(58) Field of Classification Search
CPC ............ B01J 23/63; B01J 21/46; B01J 21/02; B01J 21/066; B01J 23/002; B01J 23/10; C07C 1/0435

USPC ......... 502/302–304, 308, 325, 349, 351, 355; 585/703; 423/600, 594.12
See application file for complete search history.

(56) References Cited

U.S. PATENT DOCUMENTS 3,615,164 A   10/1971   Baker et al.
3,663,162 A    5/1972   Randhava
(Continued)

FOREIGN PATENT DOCUMENTS

DE    37 37 419          5/1988
EP    1020216 A1 *       7/2000
(Continued)

OTHER PUBLICATIONS

Betta, R. A. Dalla, et al., "Heterogeneous Methanation: Initial Rate of CO Hydrogenation on Supported Ruthenium and Nickel", Journal of Catalysis, vol. 35, No. 1, pp. 54-60, (1974).

(Continued)

Primary Examiner — Anthony J Zimmer
(74) Attorney, Agent, or Firm — Oblon, Spivak, McClelland, Maier & Neustadt, L.L.P.

(57) ABSTRACT

The invention relates to the use of a catalytic composition for selective methanization of carbon monoxide in hydrogen- and carbon dioxide-containing streams, wherein the active component used is ruthenium and the support material is a lanthanum-cerium-zirconium oxide, where the total loading of the support material with the active component is 0.1 to 20% by weight, based on the total weight of the catalytically active composition, and the support material comprises a lanthanum oxide content of 0.1 to 15% by weight, a cerium oxide content of 0.1 to 15% by weight and a zirconium oxide content of 30 to 99.8% by weight, based on the weight of the overall support material.

9 Claims, 5 Drawing Sheets

Activity and selectivity of inventive Ru catalysts in temperature screening: Performance as a function of the support

(56) References Cited

U.S. PATENT DOCUMENTS

| | | | |
|---|---|---|---|
| 4,927,799 A | 5/1990 | Matsumoto et al. | |
| 5,064,803 A * | 11/1991 | Nunan | 502/170 |
| 6,150,288 A * | 11/2000 | Suzuki et al. | 501/105 |
| 6,387,338 B1 * | 5/2002 | Anatoly et al. | 423/239.1 |
| 7,456,128 B2 * | 11/2008 | Mao | 502/208 |
| 7,939,041 B2 * | 5/2011 | Darab | 423/263 |
| 2002/0115563 A1 | 8/2002 | Blanchard et al. | |
| 2004/0175310 A1 | 9/2004 | Feaviour et al. | |
| 2005/0096211 A1 * | 5/2005 | Takeda et al. | 502/66 |
| 2005/0096212 A1 | 5/2005 | Takeda et al. | |
| 2005/0277544 A1 * | 12/2005 | Mao | 502/208 |
| 2006/0178261 A1 * | 8/2006 | Larcher et al. | 502/304 |
| 2006/0272213 A1 | 12/2006 | Feaviour et al. | |

FOREIGN PATENT DOCUMENTS

| | | | |
|---|---|---|---|
| EP | 0 946 406 | 11/2001 | |
| EP | 1 174 486 | 1/2002 | |
| EP | 1 246 286 | 10/2002 | |
| EP | 1 707 261 | 10/2006 | |
| EP | 1 712 278 | 10/2006 | |
| JP | 2002 68707 | 3/2002 | |
| JP | 2005224792 A * | 8/2005 | |
| WO | 97 43207 | 11/1997 | |
| WO | WO 2004085806 * | 10/2004 | B01D 53/94 |
| WO | 2007 043442 | 4/2007 | |

OTHER PUBLICATIONS

"Chemical abstracts", vol. 74, Section. 35106u, p. 245, (1971).

Le Page, J. F. "Handbook of Heterogeneous Catalysis: 2.5 Catalyst Forming", A Wiley Company, VCH, vol. 1, pp. 412-419, (1997).

Che, M. et al., "Handbook of Heterogeneous Catalysis: 2.2 Supported Catalysts", vol. 2, pp. 191-207, (1997).

* cited by examiner

Figure 1:
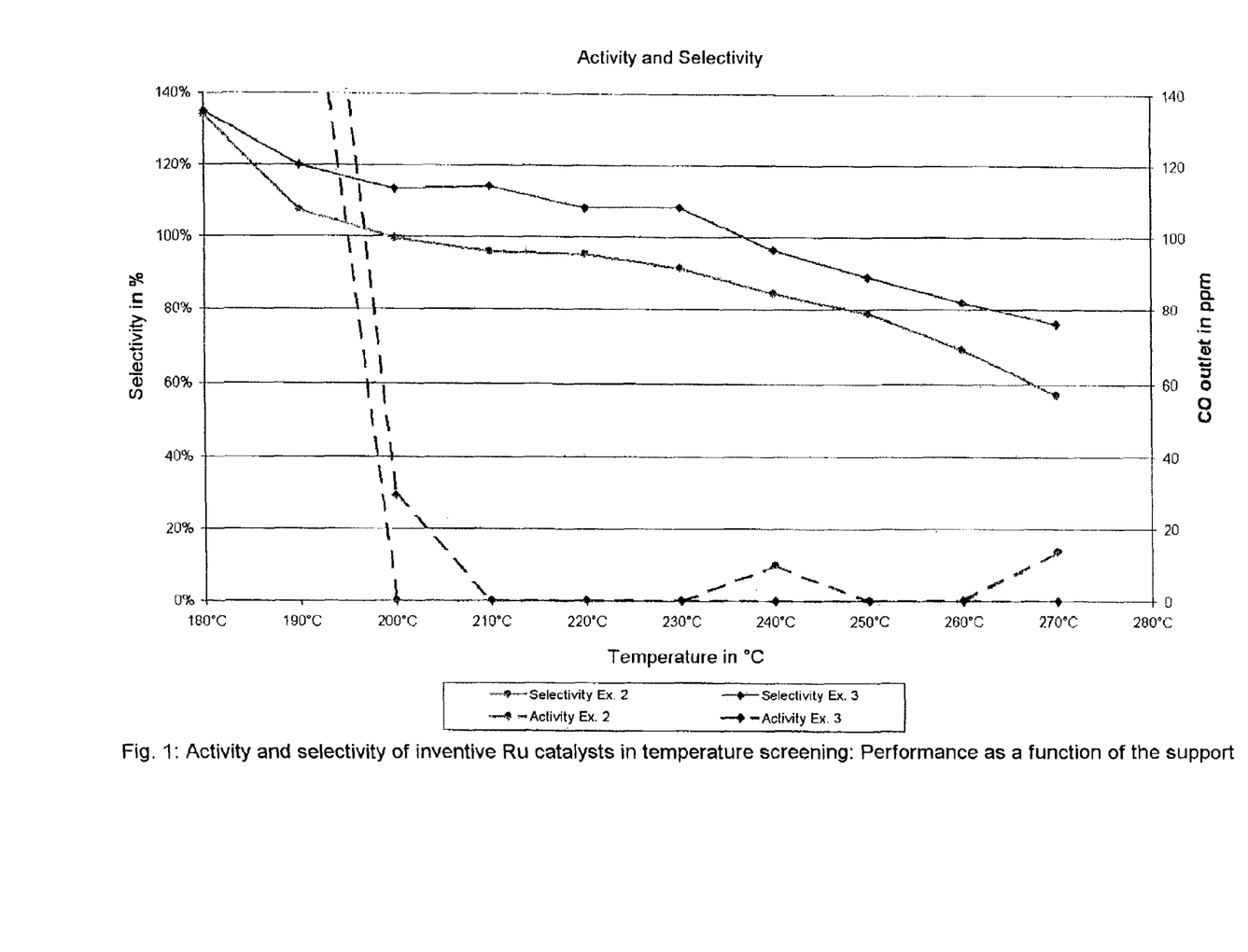

Fig. 1: Activity and selectivity of inventive Ru catalysts in temperature screening: Performance as a function of the support Fig. 2: Activity and selectivity of inventive Ru catalysts in temperature screening: Performance as a function of the Ru content.

Figure 3:
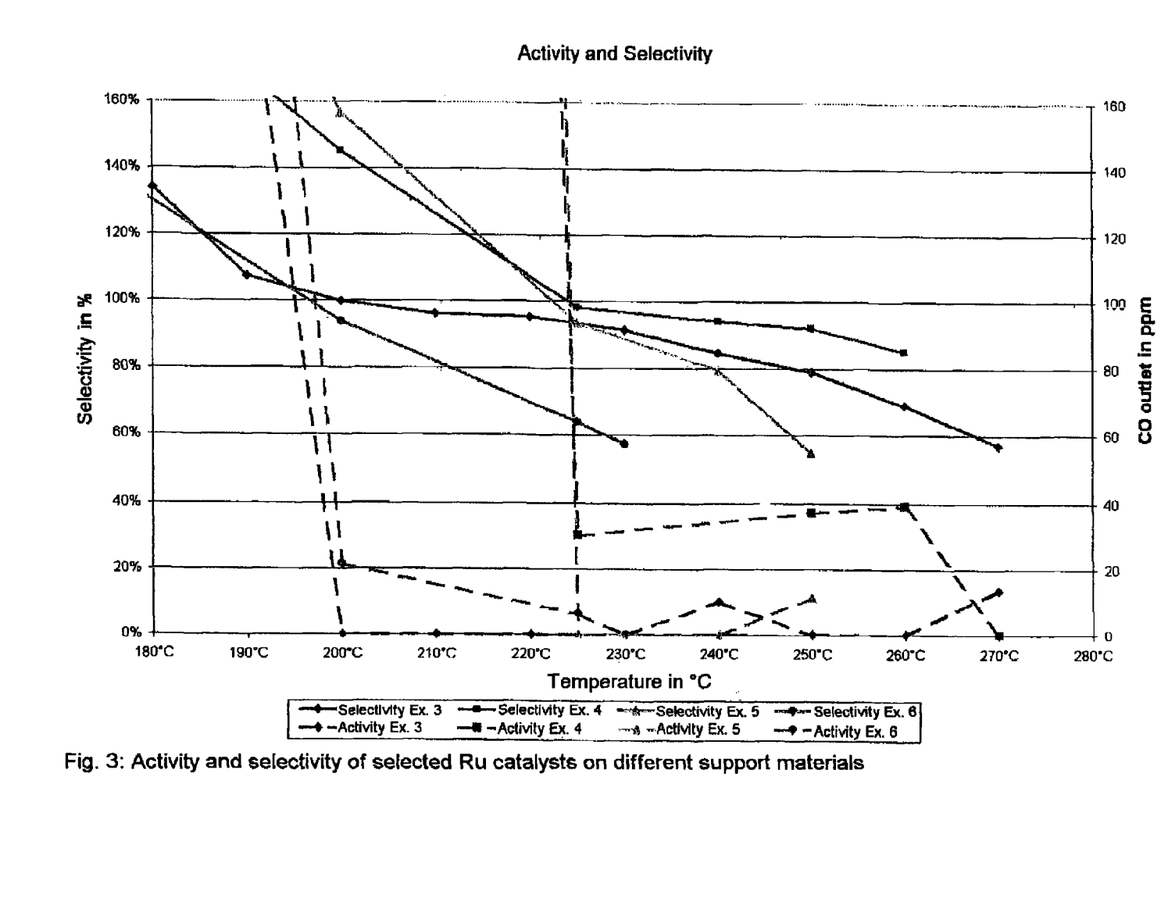

Fig. 3: Activity and selectivity of selected Ru catalysts on different support materials Fig. 4: Activity and selectivity of inventive Ru catalysts in a long-term test Fig. 5: Reworking of patents

CATALYST FOR SELECTIVE METHANIZATION OF CARBON MONOXIDE

The invention relates to the use of a catalytic composition for selective methanization of carbon monoxide in hydrogen- and carbon dioxide-containing streams, especially for use in fuel cell systems.

Low temperature PEM fuel cells (PEM=polymer electrolyte membrane) can be operated only with hydrogen or hydrogen-rich gases of a defined quality. The carbon monoxide (CO) concentration in particular is a critical parameter. It depends on the energy carrier used and on the reforming process used. The removal of relatively high CO concentrations is possible with the water gas shift reaction with further formation of hydrogen.

$$CO+H_2O \leftrightarrow CO_2+H_2 \; \Delta H=-44 \text{ kJ/mol}$$

Since this is an equilibrium reaction, depending on the process design and temperature, a residual concentration of CO remains in the gas stream, generally in the range from 0.25 to 1.5% by volume. In the case of use of catalysts with a high copper content, for example, CO removal down to 2 500 ppm can be achieved. The CO content in the hydrogen-rich gas must, however, be reduced further in order to prevent poisoning of the anode catalyst; guide values here are between not more than 10 and 50 ppm.

The level of CO present in the gas stream is typically reduced down to below the required limits in a fine purification stage. Selective oxidation is currently the most common CO removal method. Selective oxidation has a high level of development, but possesses not only the disadvantage of only moderate selectivity but also the necessity of exact metering of the air supply, which results in a high level of measurement and control complexity. If the necessary ratio of oxygen to CO is not maintained exactly, this can lead to high losses of hydrogen. Moreover, the narrow temperature window of generally not more than 20° C. requires complex heat management of the reactor. There is an additional safety problem through the addition of the oxidizing agent, oxygen, to the gas. The removal of the CO by reaction with $H_2$ (methanization) has considerable advantages over the selective CO oxidation by virtue of its undemanding implementation in terms of process technology.

CO methanization (hydrogenation of carbon monoxide to methane) proceeds according to the reaction equation:

$$CO+3H_2 \rightarrow CH_4+H_2O \; \Delta H=-206.2 \text{ kJ/mol}$$

A competing reaction which proceeds is the conversion of $CO_2$ to methane:

$$CO_2+4H_2 \rightarrow CH_4+2H_2O \; \Delta H=-164.9 \text{ kJ/mol}$$

The particular challenge for the selective CO methanization is that CO should be hydrogenated preferentially and not $CO_2$, since this would consume further hydrogen. According to the thermodynamics, CO methanization is preferred over $CO_2$ methanization. It is known that $CO_2$ methanization does not set in below a CO concentration limit of 200 to 300 ppm in the reformate. The CO concentration in the reformate is approx. 15 000 ppm, i.e. higher than the upper limit stated by a factor of 50. The $CO_2$ content of approx. 15 to 25% by volume is one order of magnitude above the CO content. Accordingly, a CO-selective catalyst is indispensible at low CO concentrations, as required, for example, for PEM fuel cells.

The selective methanization of CO has been known for some time. At first, CO was methanized over a nickel catalyst, although $CO_2$ had to be scrubbed out beforehand. In 1968, a ruthenium catalyst for selective CO methanization was claimed by Baker et al. (U.S. Pat. No. 3,615,164), which involved the use of a ruthenium or rhodium catalyst on an aluminum oxide support material. Chemical Abstracts, volume 74, 1971, 35106u likewise describes the selective methanization of CO in a gas mixture comprising hydrogen, carbon dioxide and carbon monoxide at temperatures in the range between 125 and 300° C. using ruthenium catalysts. U.S. Pat. No. 3,663,162 of 1972 claims a Raney nickel catalyst for this reaction.

In EP-A-1174486, a methanization stage is combined with a unit for selective oxidation with the aim of a lower oxygen consumption and of a lower $CO_2$ methanization rate. The catalyst used for the methanization comprises Ru, Pt, Rh, Pd or Ni on an aluminum oxide support.

In EP-A-0946406, two methanization stages of different temperature levels are connected to one another. The advantage here is said to be that only a small amount of $CO_2$, if any, methanizes in the high temperature stage, but a large proportion of the carbon monoxide is already degraded. In the subsequent low temperature methanization, the residual CO is removed. A noble metal catalyst is used, especially Rh, on an aluminum support.

WO 97/43207 describes the combination of a first stage for selective oxidation with a subsequent methanization stage with rhodium as the active component. This combination is said to allow both processes to be operated under optimal conditions.

Further, more recent applications, for example EP-A-1246286, in which, as the last process stage of a gas purification, a methanization reactor is connected downstream of a unit for selective oxidation for the reasons of simpler construction and of better handling, use conventional catalysts, predominantly based on ruthenium or nickel.

JP-A-2002/068707 discusses methanization catalysts applied to a refractory inorganic oxide selected from oxides of aluminum, titanium, silicon or zirconium.

EP-A-1707261 describes a process for selective oxidation of CO with Ru on a catalyst composed of mixed metal oxides, doped with lanthanides.

US-A-2005/0096212 describes selective methanization over a catalyst composed of Ru, Rh, Ni or combinations on β-zeolite, mordenite and faujasite. Although the desired CO concentrations below 100 ppm are achieved in this way, the selectivity at temperatures above 190° C., at which the catalyst displays its activity, falls significantly below 50%. Since the hydrogenation of $CO_2$ destroys ½ as much hydrogen per mole as the hydrogenation of CO, the requirement for maximum selectivity is very important. Moreover, a viable catalytic activity is achieved only over the very small temperature window between 170° C. and 180° C.

The prior art processes do not permit sufficient lowering of the CO content with preservation of the $CO_2$ content to be ensured. The catalysts developed to date either do not work selectively enough or are active only within a very narrow temperature range. The very narrow temperature range in particular makes industrial implementation of the "selective methanization" concept very difficult. This is because, as soon as the selectivity falls, the reactor is heated, which leads to further methanization of $CO_2$ and hence to the thermal "runaway" of the process unit. The exothermicity of the reaction thus results in hotspots. For this reason, a wide temperature window has to be operable. Equally problematic is the adiabatic temperature increase in monoliths when they are used as catalysts, which is often the case in practice.

For fuel cell applications in particular, the required maximum CO content in the hydrogen-rich gas fed in and the necessary high selectivity (methanization of CO, but not of $CO_2$) over a wide temperature window still represents great potential for development for suitable deactivation-resistant catalysts.

It was thus an object of the invention to provide a catalyst for selective CO methanization, which is selective and active within a wide temperature range.

The object is achieved in accordance with the invention by using, for the selective methanization of carbon monoxide in hydrogen- and carbon dioxide-containing streams, a catalytically active composition which comprises ruthenium as the active component and a lanthanum-cerium-zirconium oxide (LaCeZr oxide) as the support material.

A catalyst which comprises a lanthanum-cerium-zirconium oxide as the support material and ruthenium as the active component is capable of ensuring the methanization of CO within a wide temperature range in a virtually constant selectivity over a long period of time. Conventional catalysts exhibit a significant decline in selectivity with increasing temperature and prolonged run times. Employment of the inventive catalyst requires a significantly lower level of control complexity, since the temperature window in the methanization of the CO has to be complied with to a less exact degree. Furthermore, a catalyst which works well even at high temperatures can be connected directly downstream of the prepurification stage (low temperature conversion), which is operated at about 220 to 280° C.

The invention thus provides for the use of a catalytically active composition for the selective methanization of carbon monoxide in hydrogen- and carbon dioxide-containing streams, which comprises ruthenium as the active component and a lanthanum-cerium-zirconium oxide as the support material, where the total loading of the support material with the active component is 0.1 to 20% by weight, based on the total weight of the catalytically active composition, and the support material comprises a lanthanum oxide content of 0.1 to 15% by weight, a cerium oxide content of 0.1 to 15% by weight and a zirconium oxide content of 30 to 99.8% by weight, based on the weight of the overall support material.

The embodiments of the present invention can be inferred from the claims, the description and the examples. It is obvious that the features of the inventive subject matter which have been specified above and are still to be explained below are usable not just in the particular combinations specified but also in other combinations without leaving the scope of the invention.

According to the invention, the support material used is a lanthanum-cerium-zirconium oxide (LaCeZr oxide).

The support material advantageously has a lanthanum oxide content of 0.1 to 15% by weight, preferably of 5 to 15% by weight and more preferably of 10 to 15% by weight. The cerium oxide content is advantageously 0.1 to 15% by weight, preferably 0.1 to 10% by weight and more preferably 3 to 7% by weight, based in each case on the weight of the overall support material.

The zirconium oxide content of the support material is advantageously 30 to 99.8% by weight. In preferred embodiments, it is at a content which supplements the proportions by weight of the lanthanum oxide and of the cerium oxide and any further constituents, as described above, to 100% by weight in each case.

In addition to the components mentioned, the support material used in accordance with the invention may comprise further materials usable customarily in catalyst chemistry for these purposes, for example aluminum oxide. Suitable binder materials are those which have a sufficiently high BET surface area. The BET surface area of these additionally used binder materials should advantageously be at least 120 $m^2/g$. The content of these further materials should not exceed 30% by weight, preferably 20% by weight, based in each case on the weight of the overall support material.

The catalytically active composition comprises ruthenium as the active component. The active component is preferably present in the catalyst as the oxide. The actual active material is then generated in situ by activation with hydrogen.

The loading of the support material with the active ruthenium components is advantageously 0.1 to 20% by weight, preferably 0.1 to 10% by weight and more preferably 0.1 to 5% by weight. Further advantageous ranges are, for example, 1 to 10% by weight, 1 to 5% by weight, and also 2 to 5 and 3 to 5% by weight. The figures are based in each case on the total weight of the catalytically active composition.

A preferred composition of the catalytically active system comprises, on a lanthanum-cerium-zirconium oxide support with a lanthanum oxide content of 0.1 to 15% by weight and a cerium oxide content of 0.1 to 15% by weight, based in each case on the weight of the entire support material, 0.1 to 20% by weight of Ru, based on the total weight of the catalytically active composition.

A further preferred composition of the catalytically active system comprises, on a lanthanum-cerium-zirconium oxide support with a lanthanum oxide content of 0.1 to 15% by weight and a cerium oxide content of 0.1 to 15% by weight, based in each case on the weight of the entire support material, 2 to 5% by weight of Ru, based on the total weight of the catalytically active composition.

A further preferred composition of the catalytically active system comprises, on a lanthanum-cerium-zirconium oxide support with a lanthanum oxide content of 0.1 to 15% by weight and a cerium oxide content of 0.1 to 10% by weight, based in each case on the weight of the entire support material, 3 to 5% by weight of Ru, based on the total weight of the catalytically active composition.

A particularly preferred composition of the catalytically active system comprises, on a lanthanum-cerium-zirconium oxide support with a lanthanum oxide content of 10 to 15% by weight and a cerium oxide content of 3 to 7% by weight, based in each case on the weight of the entire support material, 3 to 5% by weight of Ru, based on the total weight of the catalytically active composition.

Further embodiments in the composition of the catalyst used in accordance with the invention can be inferred from the examples. It is obvious that the features of the catalyst which have been specified above and are still to be stated below are usable not just in the specified combinations and value ranges but also in other combinations and value ranges within the limits of the main claim, without leaving the scope of the invention.

In addition, the active component and/or the support material can be doped in small amounts with further elements which are usable for these purposes and are known to those skilled in the art, without leaving the scope of the invention.

The catalyst used in accordance with the invention is prepared in a customary manner, for example by dissolving the active component and any doping elements, preferably in the form of their salts/hydrates, and then applying them in a suitable manner, for example by impregnation, to the lanthanum-cerium-zirconium oxide support. Thereafter, the catalyst is dried, calcined, reduced if appropriate and passivated if appropriate.

The active components can be applied in a customary manner to the support material by impregnation, for example as a washcoat to a monolith. The procedure and process conditions are described, for example, in the Handbook of heterogeneous catalysis, Vol. 1, VCH Verlagsgesellschaft Weinheim, 1997.

An alternative mode of preparation comprises the kneading of the support materials with the salts/hydrates of the active elements and any doping elements with subsequent extrusion, drying and calcination if appropriate, reduction if appropriate and passivation if appropriate.

The kneading of the support material with the active materials and the further steps can be effected in a customary manner with known apparatus.

Shaped bodies can be produced from pulverulent raw materials by customary methods known to those skilled in the art, for example tableting, aggregation or extrusion, as described in references including the Handbook of Heterogeneous Catalysis, Vol. 1, VCH Verlagsgesellschaft Weinheim, 1997.

In the shaping or the application, assistants known to those skilled in the art, such as binders, lubricants and/or solvents, can be added.

This gives rise to a catalytically active composition which is outstandingly suitable for the selective methanization of carbon monoxide in hydrogen- and carbon dioxide-containing streams. Depending on the particular reaction conditions, this achieves the desired significant depletion of CO to less than 10 ppm in the gas mixture with minimal loss of hydrogen.

Advantageously, the selective methanization of the CO is thus achieved within a temperature range from preferably 100 to 300° C.

The selective methanization of CO in a temperature range from 180 to 260° C. is particularly advantageous. This temperature enables direct thermal integration with the upstream low temperature conversion. It thus becomes possible to couple the inventive methanization stage directly onto the low temperature conversion stage. The high activity with equally high CO selectivity within this temperature range ensures that stable and in particular thermally integrated operation of the catalyst becomes possible at all.

The catalytically active composition is thus outstandingly suitable for CO fine purifications in hydrogen- and carbon dioxide-containing streams, more particularly for use in the generation of hydrogen for fuel cell applications.

The invention is illustrated in detail by the examples which follow, but without undertaking a corresponding limitation thereby.

EXAMPLES

Example 1

206.3 g of $ZrO_2$, 29.6 g of $La_2(NO_3)_2$, 0.24 g of $CeO_2$ and 31.3 g of aluminum oxide hydroxide (Pural SB) were mixed in a kneader and acidified with dilute $HNO_3$. A sufficient amount of water to give rise to an extrudable material was added. The shaped extrudates were dried and calcined. Thereafter, this support was admixed with a $RuCl_3$ solution whose concentration was such that the end product, calcined once again, bore 3% by weight of Ru as the active material.

Example 2

279.8 g of $ZrO_2$, 12.5 g of $CeO_2$, 31.5 g $La_2(NO_3)_2$ and 33.3 g of aluminum oxide hydroxide (Pural SB) were used to produce a support material as described in example 1. Thereafter, this support was admixed with a $RuCl_3$ solution whose concentration was such that the end product, calcined once again, bore 3% by weight of Ru as the active material.

Example 3

A support composed of 70% by weight of $ZrO_2$, 15% by weight of $CeO_2$, 5% by weight of $La_2O_3$ and 10% by weight of $Al_2O_3$ was admixed with a $RuCl_3$ solution whose concentration was such that the end product, calcined once again, bore 3% by weight of Ru as the active material.

Example 4

Comparative Example 37.5 g of PZ2-25H(H-ZSM-5, MFI structure type, from Zeochem, modulus=25) were initially charged with 11.8 g of aluminum oxide hydroxide (Versa 250, from UOP) in a kneader, and corroded slightly with formic acid. The mixture was admixed with water, extruded and calcined. Thereafter, this support was impregnated with a solution of ruthenium chloride hydrate and lanthanum nitrate which was such that the end product comprised 3% by weight of Ru and 5% by weight of La. The extrudates were dried and calcined.

Example 5

Comparative Example 100 g of PZ2-25H(H-ZSM-5, MFI structure type, from Zeochem, modulus=25) were initially charged with 35.6 g of aluminum oxide hydroxide (Pural SB), and corroded slightly with formic acid. The mixture was admixed with water, ruthenium chloride hydrate and iron chloride hydrate, and extruded. After calcination, the end product comprised 3% by weight of Ru and 1% by weight of Fe.

Example 6

Comparative Example

Testing of a commercially available methanization catalyst with 5% Ru on $TiO_2$.

Example 7a-d

A support composed of 70% by weight of $ZrO_2$, 15% by weight of $CeO_2$, 5% by weight of $La_2O_3$ and 10% by weight of $Al_2O_3$ was admixed with an $RuCl_3$ solution whose concentration was such that the end product, calcined once again, bore 5% by weight of Ru (example 7a), 4% by weight of Ru (example 7b), 3% by weight of Ru (example 7c) or 2% by weight of Ru (example 7d) as the active material.

Example 8

Reworking of Patent US 2005/096211

150 g of TZB 213 (β-zeolite, from Süd-Chemie/Tricat, modulus=12) were initially charged with 50 g of aluminum oxide hydroxide (Pural SB) in a kneader and corroded slightly with formic acid. The mixture was admixed with water, extruded and calcined. Thereafter, this support was impregnated with a solution of ruthenium nitrosylnitrate which was such that the end product comprised 3% by weight of Ru. The extrudates were dried and calcined.

Example 9

Reworking of Patent JP 2002/068707

432.8 g of ZrOz powder were initially charged with 12 g of methylcellulose (Walocel, from Wolff Cellulosics) in a kneader, and corroded slightly with nitric acid. The mixture was admixed with water and ruthenium chloride hydrate solution, and extruded. After calcination, the end product comprised 3% by weight of Ru.

Example 10

Reworking of Patent JP 2002/068707

250 g of aluminum oxide hydroxide (Pural SB) were initially charged in a kneader and corroded slightly with formic acid. The mixture was admixed with water and ruthenium chloride hydrate solution and extruded. After calcination, the end product comprised 3% by weight of Ru.

Example 11

Reworking of Patent JP 2002/068707

235.5 g of $TiO_2$ powder were initially charged in a kneader and corroded slightly with formic acid. The mixture was admixed with water and ruthenium chloride hydrate solution, and extruded. After calcination, the end product comprised 3% by weight of Ru.

Test Conditions:

For the experiment, an electrically heated tubular reactor with a volume of 50 ml and a diameter of 14 mm was used.

At the bottom, 4 ml of steatite spheres with a diameter of 1.8 to 2.2 mm were installed, onto which the catalyst mixture was subsequently introduced. The catalyst mixture consisted of approx. 20 ml of catalyst which had been mixed thoroughly with approx. 10 ml of steatite spheres with a diameter of 1.8 to 2.2 mm. The preliminary bed used was 14 ml of steatite spheres with a diameter of 1.8 to 2.2 mm, which filled the remaining volume of the reactor.

The catalyst was first reduced with 90 l/h of nitrogen and 10 l/h of hydrogen at 230° C. for one hour. The gas composition selected for the experiment is typical of the output of the low temperature shift stage after the reforming of methane, and was 33% by volume of $H_2$, 28% by volume of $N_2$, 25% by volume of $H_2O$, 13% by volume of $CO_2$, 0.5% by volume of CO and 0.5% by volume of $CH_4$. A loading of 5000 $l \cdot h^{-1} \cdot l^{-1}{}_{cat}$ was selected.

Once all gases had been set and the reactor (after the reduction at 230° C.) had been cooled to 150° C., the experiment was started. Every three hours, the temperature was increased stepwise; the maximum temperature was 300° C. The concentration of the gases was determined downstream of the reactor by means of GC and IR.

The catalysts were analyzed under the conditions specified.

A selectivity greater than 60% was considered to be satisfactory. The selectivity falls with rising temperature. Table 1 below reports in each case the temperatures at which the selectivity goes below this parameter and the temperature from which CO is depleted to below 10 ppm. The last column reports the size of the temperature window in which both sufficient activity (which leads to less than 10 ppm of CO downstream of the reactor) and sufficient selectivity (>60%) are achieved.

TABLE 1

List of selected and tested catalysts

| Catalyst | Active material Support | Temperature [° C.], from which Selectivity <60% | Temperature [° C.], from which Activity CO < 10 ppm | Temperature range [K], with CO <10 ppm and selectivity >60% |
|---|---|---|---|---|
| Example 1: | 3% Ru LaCeZr oxide (type I) | >260 | 210 | >50 |
| Example 2: | 3% Ru LaCeZr oxide (type II) | >260 | 210 | >50 |
| Example 3: | 3% Ru LaCeZr oxide (type III) | 265 | 200 | 65 |
| Example 4: | 3% Ru and 5% La ZSM-5 zeolite | >260 | —* | 0 |
| Example 5: | 3% Ru and 1% Fe ZSM-5 zeolite | 245 | 225 | 20 |
| Example 6: | 5% Ru $TiO_2$ | 225 | —* | 0 |
| Example 7a: | 5% Ru LaCeZr oxide (type III) | 245 | 175 | 70, |
| Example 7b: | 4% Ru LaCeZr oxide (type III) | 245 | 190 | 55 |
| Example 7c: | 3% Ru LaCeZr oxide (type III) | 265 | 200 | 65 |
| Example 7d: | 2% Ru LaCeZr oxide (type III) | >280 | 220 | >60 |
| Example 8 | 3% Ru β-zeolite | >260 | 220 | 40 |
| Example 9 | 3% Ru $ZrO_2$ | 200 | 200 | 0 |
| Example 10 | 3% Ru $Al_2O_3$ | >260 | —* | 0 |
| Example 11 | 3% Ru $TiO_2$ | — | —* | 0 |

*Target value of 10 ppm is not attained

FIG. 1 shows the activity and selectivity of selected Ru catalysts in the temperature screening (performance as a function of different $LaCeZrO_x$ support with the same Ru content). The broad temperature range in which the catalysts used in accordance with the invention exhibit full CO conversion while maintaining the necessary high selectivity is evident.

Figure 2:
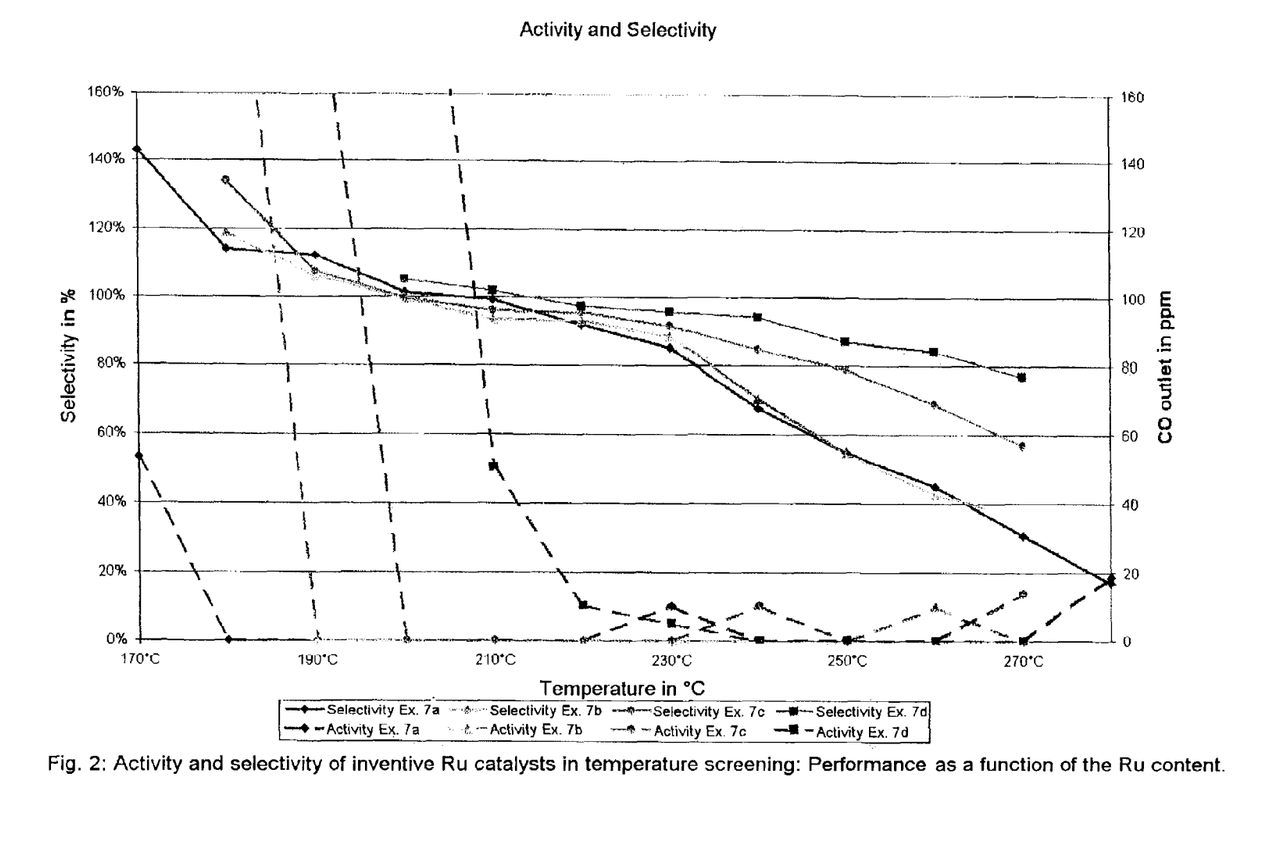

FIG. 2 shows the activity and selectivity of selected Ru catalysts in the temperature screening (performance as a function of the Ru content). The influence of the Ru concentration on the activity range of the individual catalysts while maintaining a high selectivity is evident.

FIG. 3 shows the activity and selectivity of selected Ru catalysts on different support materials. This demonstrates the superiority of the catalyst used in accordance with the invention based on lanthanum-cerium-zirconium oxide as a support material over prior art catalysts.

Figure 4:
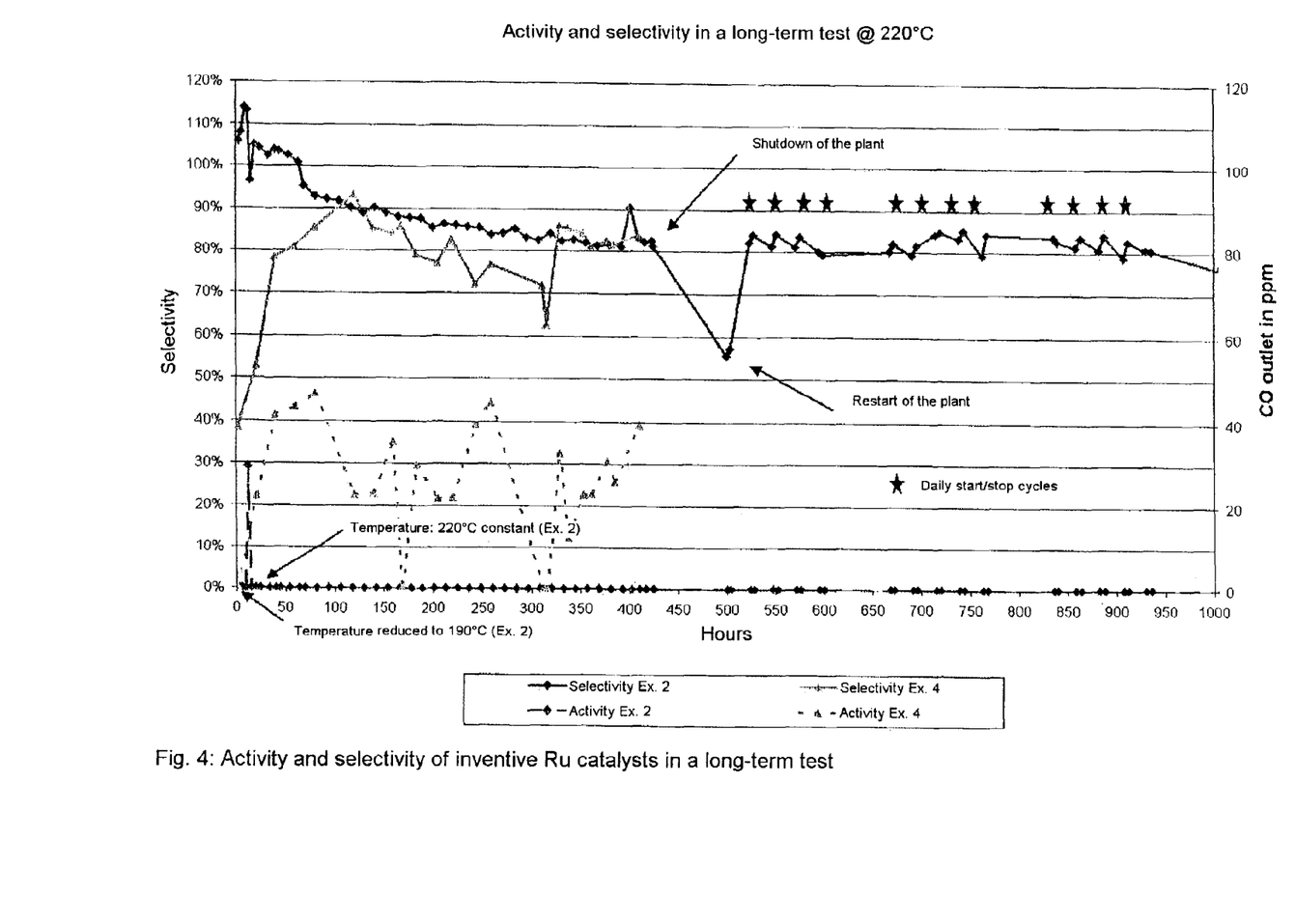

FIG. 4 shows activity and selectivity of selected Ru catalysts in a long-term test.

Figure 5:
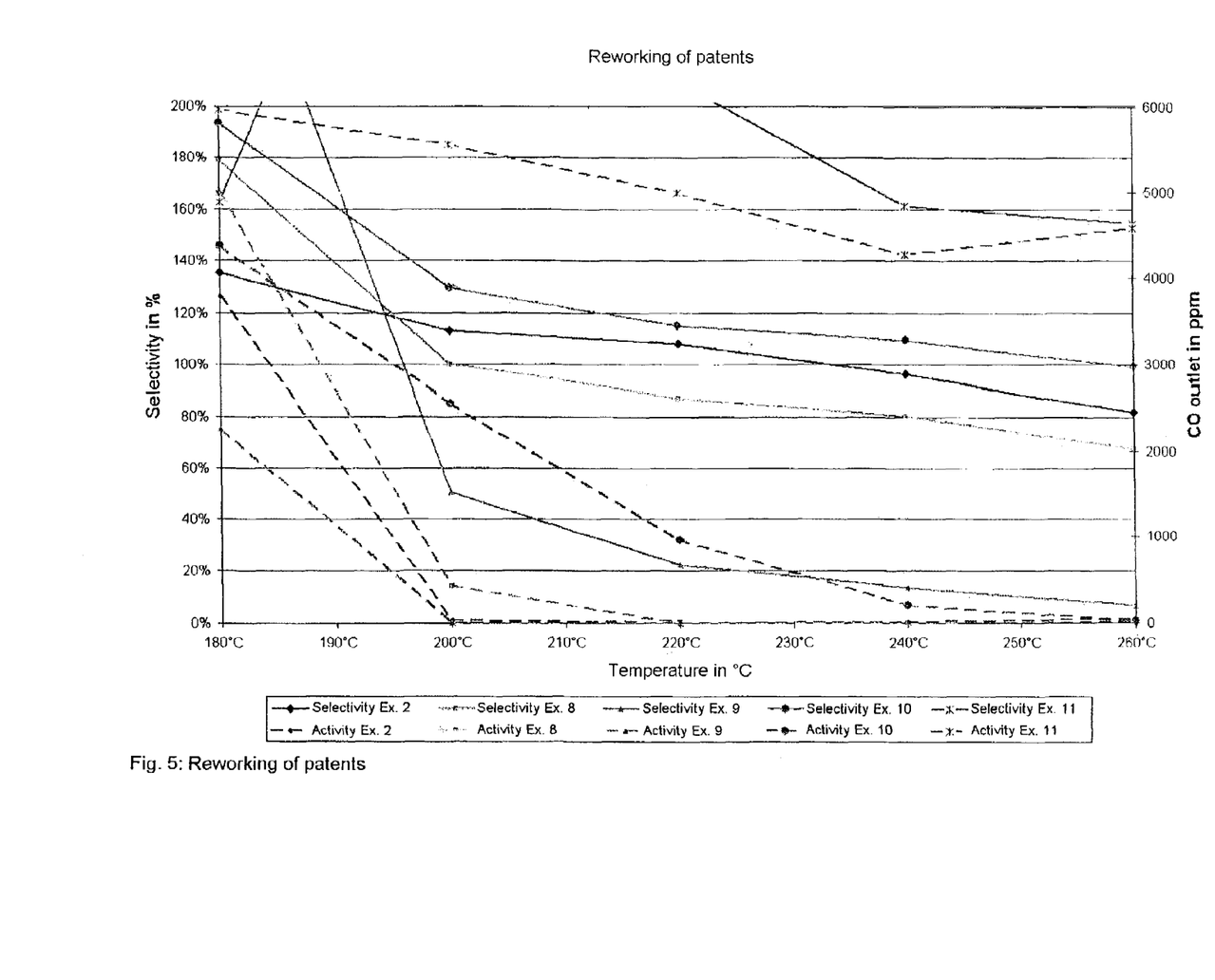

FIG. 5 demonstrates the significantly higher activity and selectivity of the catalyst used in accordance with the invention compared to the prior art and existing patent applications.

The invention claimed is:

1. A catalytically active composition for the selective methanization of carbon monoxide in hydrogen and carbon dioxide-containing streams comprising ruthenium as an active component and a lanthanum-cerium-zirconium-aluminum oxide as a support material, where the total loading of the support material with the active component is 0.1 to 20% by weight, based on the total weight of the catalytically active composition, and the support material comprises a lanthanum oxide content of 0.1 to 15% by weight, a cerium oxide content of 0.1 to 15% by weight a zirconium oxide content of 70 to 99.8% by weight, the sum of the lanthanum, cerium and zirconium oxides being 100% by weight, and an aluminum oxide content not exceeding 30% by weight, based on the weight of the overall support material.

2. The catalytically active composition according to claim 1, wherein the total loading of the support material with the active component is 0.1 to 10% by weight, based on the total weight of the catalytically active composition.

3. The catalytically active composition according to claim 1, wherein the total loading of the support material with the active component is 2 to 5% by weight, based on the total weight of the catalytically active composition.

4. The catalytically active composition according to claim 1, wherein the catalytically active composition comprises a lanthanum-cerium-zirconium-aluminum oxide support with a lanthanum oxide content of 10 to 15% by weight and a cerium oxide content of 3 to 7% by weight, based in each case on the weight of the overall support material, and 2 to 5% by weight of ruthenium, based on the total weight of the catalytically active composition.

5. The catalytically active composition according to claim 1, wherein the total loading of the support material with the active component is 0.1 to 5% by weight, based on the total weight of the catalytically active composition.

6. The catalytically active composition according to claim 1, wherein the total loading of the support material with the active component is 1 to 10% by weight, based on the total weight of the catalytically active composition.

7. The catalytically active composition according to claim 1, wherein the total loading of the support material with the active component is 1 to 5% by weight, based on the total weight of the catalytically active composition.

8. The catalytically active composition according to claim 1, wherein the aluminum oxide content does not exceed 20% by weight.

9. The catalytically active composition according to claim 1, which is obtained by either (1) mixing precursor components of the support material and calcining the precursor components to form the support material, mixing with a precursor solution of the active component, and then calcining again, or (2) mixing components of the support material with a precursor solution of the active component and then calcining.

* * * * *